United States Patent [19]

Gorun et al.

[11] Patent Number: 5,041,575

[45] Date of Patent: Aug. 20, 1991

[54] MANGANESE OLIGOMER CONTAINING MAIN GROUP ELEMENTS

[75] Inventors: Sergiu M. Gorun, Upper Montclair; Robert T. Stibrany, Long Valley, both of N.J.

[73] Assignee: Exxon Research and Engineering Company, Florham Park, N.J.

[21] Appl. No.: 580,413

[22] Filed: Sep. 10, 1990

[51] Int. Cl.$^5$ .................. C07F 13/00; C07F 3/00
[52] U.S. Cl. ........................ 556/28; 556/45; 556/46; 556/50; 423/605
[58] Field of Search .............. 556/28, 45, 46, 50; 423/605

[56] References Cited

U.S. PATENT DOCUMENTS

| | | | |
|---|---|---|---|
| 4,207,245 | 6/1980 | Halbert | 556/28 |
| 4,730,064 | 3/1988 | Halbert et al. | 556/28 X |
| 4,937,338 | 6/1990 | Flohr et al. | 556/28 X |

*Primary Examiner*—Arthur C. Prescott
*Attorney, Agent, or Firm*—Joseph J. Dvorak

[57] ABSTRACT

The present invention is based on the discovery that the previously disclosed tetranuclear manganese compounds are converted into a hexadeca manganese aggregate and a core of 4 barium, 2 sodium and 1 chloride ion. Stated differently, one embodiment of the present invention comprises a composition of matter having the formula:

$$[Mn_{16}Ba_8Na_2ClO_4(OH)_4(CO_3)_4(H_2O)_{22}L_8]\cdot xH_2O$$

wherein x is an integer ranging from 0 to about 32 and L is a ligand having the formula:

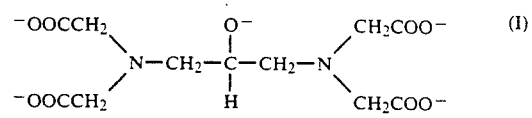

Another embodiment of the present invention comprises a method of preparing the novel compounds of the present invention, which method comprises preparing an aqueous solution containing sodium chloride, a source of carbonate ion selected from sodium carbonate, sodium bicarbonate and mixtures thereof and a compound having the formula:

$$Ba_2[Mn_4(O)(OH)(O_2CR)_2L_2]$$

wherein R is hydrogen or a hydrocarbyl group and L is a ligand having formula I set forth above, and thereafter allowing the reaction mixture to stand for a time sufficient for a compound having the formula:

$$[Mn_{16}Ba_8Na_2ClO_4(OH)_4(CO_3)_4(H_2O)_{22}L_8]\cdot xH_2O$$

to form.

11 Claims, 1 Drawing Sheet

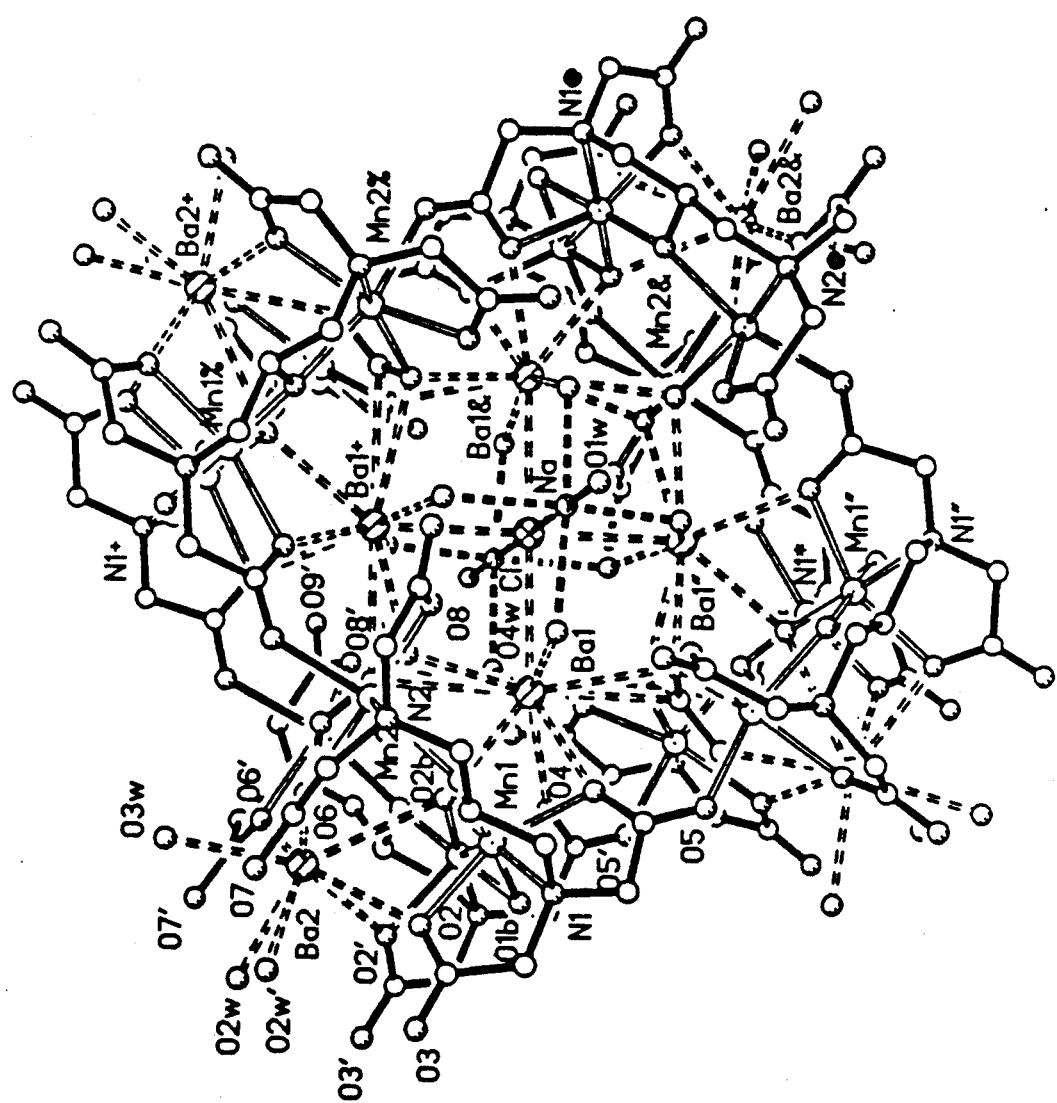

MANGANESE OLIGOMER CONTAINING MAIN GROUP ELEMENTS

FIELD OF THE INVENTION

This invention relates to novel compositions of matter and their method of preparation. More specifically, this invention relates to novel compounds including 16 manganese ions and a core of 4 barium, 2 sodium ions and a chloride ion.

BACKGROUND OF THE INVENTION

In co-pending application Ser. No. 541,699, filed June 21, 1990, there is disclosed a composition of matter having the formula $M_2[Mn_4(O)(OH)(O_2CR)_2L_2]$ wherein M is an alkali earth metal selected from magnesium, calcium, strontium, barium or mixtures thereof, R is hydrogen or a hydrocarbyl group, and L is a ligand having the formula:

$$\text{}^-OOCCH_2\diagdown \qquad\qquad O^- \qquad\qquad \diagup CH_2COO^- \qquad (I)$$
$$\diagup N-CH_2-\underset{\underset{H}{|}}{\overset{\overset{|}{}}{C}}-CH_2-N\diagdown$$
$$\text{}^-OOCCH_2 \qquad\qquad\qquad\qquad CH_2COO^-$$

These compounds have been shown to have a core structure of 4 manganese atoms which are bridged by oxo and hydroxo groups and, hence, they are referred to as oxo (hydroxo) bridged tetranuclear manganese compounds.

SUMMARY OF THE INVENTION

The present invention is based on the discovery that the previously disclosed tetranuclear manganese compounds are converted into a hexadeca manganese aggregate and a core of 4 barium, 2 sodium and 1 chloride ion. Stated differently, one embodiment of the present invention comprises a composition of matter having the formula:

$$[Mn_{16}Ba_8Na_2ClO_4(OH)_4(CO_3)_4(H_2O)_{22}L_8]\cdot xH_2O$$

wherein x is an integer ranging from 0 to about 32 and L is a ligand having the formula:

$$\text{}^-OOCCH_2\diagdown \qquad\qquad O^- \qquad\qquad \diagup CH_2COO^- \qquad (I)$$
$$\diagup N-CH_2-\underset{\underset{H}{|}}{\overset{\overset{|}{}}{C}}-CH_2-N\diagdown$$
$$\text{}^-OOCCH_2 \qquad\qquad\qquad\qquad CH_2COO^-$$

Another embodiment of the present invention comprises a method of preparing the novel compounds of the present invention, which method comprises preparing an aqueous solution containing sodium chloride, a source of carbonate ion selected from sodium carbonate, sodium bicarbonate and mixtures thereof and a compound having the formula:

$$Ba_2[Mn_4(O)(OH)(O_2CR)_2L_2]$$

wherein R is hydrogen or a hydrocarbyl group and L is a ligand having formula I set forth above, and thereafter allowing the reaction mixture to stand for a time sufficient for a compound having the formula:

$$[Mn_{16}Ba_8Na_2ClO_4(OH)_4(CO_3)_4(H_2O)_{22}L_8]\cdot xH_2O$$

to form.

The compounds of the present invention have magnetic properties rendering them particularly suitable for use in magnetic thermometry and magnetic fluids.

BRIEF DESCRIPTION OF THE DRAWINGS

The accompanying figure is a perspective illustration of the structural arrangement of a novel compound of the present invention in which, for purposes of clarity, hydrogen atoms have been omitted; non-hydrogen atoms have been represented by arbitrary-sized spheres; the bonds between Mn and its coordinated atoms are represented by double lines; the bonds between Ba and its coordinated atoms are represented by dashed double lines; the bonds between Na and its coordinated atoms are represented by dashed solid lines; and the atoms labeled with additional indicia; e.g., ', *, ", +, &, and @, are related by symmetry.

DETAILED DESCRIPTION OF THE INVENTION

The compounds of the present invention have the formula:

$$[Mn_{16}Ba_8Na_2ClO_4(OH)_4(CO_3)_4(H_2O)_{22}L_8]\cdot xH_2O$$

wherein x is an integer indicating the amount of water of crystallization, and as such, may vary over a broad range, for example, in the range of 0 to about 32, and L is a ligand having formula I set forth above. Preferably, x is an integer in the range of from about 16 to about 31.

As is shown in the figure, these novel compounds have a core structure of 4 barium and 2 sodium ions surrounding a chloride ion. These ions are referred to as main group elements. This main group element core is surrounded by 16 manganese ions.

The structure of the compounds of the present invention has been determined by well-known single crystal x-ray diffraction techniques.

The compounds of the present invention are prepared by combining an aqueous solution of sodium chloride, a source of carbonate ion such as sodium carbonate or sodium bicarbonate and a compound having the formula:

$$Ba_2[Mn_4(O)(OH)(O_2CR)_2L_2]a$$

wherein R is hydrogen or a hydrocarbyl group, especially alkyl, aryl and aralkyl groups and, preferably, R is an alkyl group having from 1 to about 30 carbon atoms. More preferably, R has from 1 to about 10 carbon atoms, and when R is an aralkyl group, it preferably will have from 7 to about 10 carbon atoms. L is a ligand having the formula (I) shown previously.

The mole ratio of the tetranuclear manganese compound to sodium chloride used generally will be in the range of from about 1:0.25 to 1:25 and, preferably, in the range of from about 1:10 to about 1:15. The mole ratio of tetranuclear manganese compound to carbonate source (e.g., sodium hydrogen carbonate) used generally will be in the range of from about 1:1 to 1:100 and, preferably, from about 1:10 to about 1:20.

It should be readily appreciated that the tetranuclear compound can be prepared and used in situ and that it is not necessary to first prepare and isolate the tetranuclear compound.

The temperature at which the combined solution is maintained is not critical. Indeed, temperatures of from about 0° C. to about 150° C. may be used, but it is most convenient and preferred to combine the reactants in water at ambient room temperature, and maintain the mixture at that temperature.

The combined solution is then allowed to stand for a time sufficient for the formation of the desired compound. Typically, crystals of the compounds of the present invention form after the combined solution has been allowed to stand overnight. Alternatively, crystallization can be hastened by known techniques such as reducing the volume of solvent by evaporation, seeding the liquid phase and the like.

The crystalline hexadecanuclear manganese compound is readily separated from the aqueous solution by decantation or filtration. The value of x in the product compound, i.e., the amount of water of hydration, will, of course, depend on the extent of drying of the product. Consequently, x will vary broadly, for example, from about 0 to about 32.

The tetranuclear manganese complex used in preparing the novel compound of the present invention is prepared by combining an aqueous containing solution of the compound having the formula:

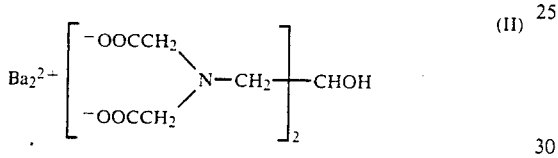

(II)

with manganese (II) carboxylate $Mn(O_2CR)_2$ or a water-soluble manganese (II) salt and a source of carboxylate $RCO_2^-$ in which R is hydrogen or a hydrocarbyl group and thereafter oxidizing the mixture to form the tetranuclear manganese compound. Exemplary hydrocarbyl groups for R include alkyl groups, aryl groups and aralkyl groups, and when R is an alkyl group, it will generally have from about 1 to 30 carbon atoms and, preferably, from 1 to 10 carbon atoms. When R is an aralkyl group, it will generally have from about 7 to about 10 carbon atoms.

Exemplary manganese (II) salts suitable for use in preparing the tetranuclear manganese compound include manganese chloride, manganese bromide, manganese nitrate, manganese tetrafluoroborate and manganese sulfate.

Exemplary sources of carboxylate include carboxylic acids and alkali metal salts of carboxylic acids.

Among suitable aqueous solutions are water, water-alcohol and water-dimethyl formamide mixtures. In general, it is particularly preferred to use water as the solvent in the preparation of the tetranuclear manganese complex.

The mole ratio of the barium compound (formula II above) to manganese (II) carboxylate or manganese (II) salt generally will be in the range of about 1:1 to about 1:3 and, preferably, about 1:2.

The hexadecanuclear manganese compounds of the present invention have a magnetic susceptibility above 100° K., which follows the Curie-Weiss law with $\theta = -7°$ K. This magnetic property renders the compounds of the present invention eminently suitable for use in magnetic thermometry and in magnetic fluids.

EXAMPLES

In the examples which follow, DHPTA refers to 1,3-diamino-2-hydroxypropane-N,N,N'N'-tetraacetic acid, the deprotonated form of which is shown previously as formula I.

EXAMPLE 1

Preparation of $Ba_2[Mn_4(O)(OH)(O_2CCH_3)_2L_2]$

In a 50 mL flask containing 5 mL of $H_2O$, 100 mgs of $Ba(OH)_2$ were neutralized with concentrated HCl to pH7. Then 445 mgs of $Mn(O_2CCH_3)_2 \cdot 4H_2O$ were added, along with 10 mL of 1:1 $H_2O$/MeOH. In another 50 mL flask, 268 mgs of DHPTA were added to 10 mL of $H_2O$. This was neutralized with solid $Ba(OH)_2$ while stirring. The two solutions were mixed together and stirred about 10 minutes, after which the pH was adjusted to 8.0 using $Ba(OH)_2$ solid. Next, ½ mL of 30% $H_2O_2$ was added dropwise. Then 5 mL of DMF were added. The mixture was stirred 10 minutes, filtered and the filtrate allowed to stand at ambient temperature while the product crystallized as the solvent evaporated. The solid tetranuclear manganese compound was separated by decanting the liquid and characterized by chemical and x-ray analysis.

EXAMPLE 2

Preparation of the $Mn_{16}$ Aggregate of This Invention

To 7 mL of an aqueous NaCl solution containing 50 mgs NaCl were added 100 mgs of $Ba_2[Mn_4(O)(OH)(O_2CCH_3)_2L_2]$ prepared according to Example 1. After all the solids dissolved, 3 mLs of an aqueous solution containing 100 mgs $NaHCO_3$ were added. Green crystals formed upon standing overnight. The crystals were separated by filtration and subjected to chemical analysis. The results of chemical analysis are:

Calculated for $[Mn_{16}Ba_8O_4(OH)_4(H_2O)_{22}L_8] \cdot 16H_2O$ (Observed) % Cl: 0.63 (0.74); % C: 19.57 (19.67); % H: 3.18 (3.17); % N: 3.97 (3.94).

Additionally, the ratio of Ba to Mn was determined by inductively coupled plasma atomic emission spectroscopy (ICPE). The results are: Calculated (Observed): 1.25 (1.33). Finally, the product was subjected to x-ray analysis and the structure (see the figure) was determined using standard x-ray techniques.

EXAMPLE 3

In Situ Preparation of the $Mn_{16}$ Aggregates

To a 50 mL aqueous solution containing 268 mgs of DHPTA brought to a pH of 8 by addition of 10 mL of $Ba(OH)_2$ solution were added 445 mgs of manganous acetate and 200 mgs of NaCl dissolved in a water/methanol mixture (volume ration 2:3). After stirring for 10 minutes, 0.5 mL of a 30% aqueous solution of $H_2O_2$ were added slowly. Then 200 mgs of $NaHCO_3$ were added to the mixture. A green crystalline solid formed on standing overnight. The crystalline solid was separated and was found by x-ray analysis to be the same as the product formed in Example 2.

EXAMPLE 4

In Situ Preparation of the $Mn_{16}$ Aggregate

The procedure of Example 3 was repeated, except that 200 mgs of $Na_2CO_3$ were added in lieu of the $NaHCO_3$. The green crystalline solid was characterized by x-ray diffraction analysis to be consistent with the products prepared in Examples 2 and 3.

What is claimed is:

1. A composition of matter having the formula:

$[Mn_{16}Ba_8Na_2ClO_4(OH)_4(CO_3)_4(H_2O)_{22}L_8] \cdot xH_2O$ wherein x is an integer ranging from 0 to about 32 and L is a ligand having the formula

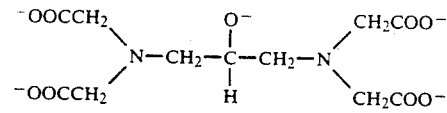

2. The composition of claim 1 wherein x is in the range of from about 16 to about 31.

3. The composition of claim 1 wherein x is 16.

4. The composition of claim 1 wherein the 16 manganese ions surround a core of the 4 barium ions, the 2 sodium ions and the 1 chloride ion.

5. A hexadecanuclear manganese aggregate including a core of 4 barium ions, 2 sodium ions and 1 chloride ion and in which the core is surrounded by 16 manganese ions.

6. A method for preparing a compound having the formula:

$[Mn_{16}Ba_8Na_2ClO_4(OH)_4(CO_3)_4(H_2O)_{22}L_8] \cdot xH_2O$ wherein x is an integer of from 0 to about 32 and L is a ligand having the formula:

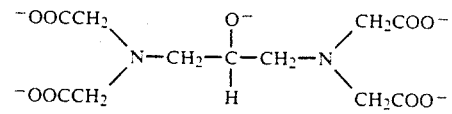

comprising:
forming an aqueous solution containing NaCl, a source of $CO_3^=$ and a compound having the formula:

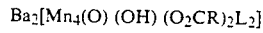

wherein R is hydrogen or a hydrocarbyl group and L is a ligand having the formula above;
allowing the solution to stand for a time sufficient for the compound to form.

7. The method of claim 6 wherein the source of $CO_3^=$ is selected from the group consisting of $Na_2CO_3$, $NaHCO_3$ and mixtures thereof.

8. The method of claim 7 wherein the mole ratio of $Ba_2[Mn_4(O)(OH)(O_2CR)_2L_2]$ to NaCl is in the range of from about 1:0.25 to about 1:25.

9. The method of claim 8 wherein the mole ratio of $Ba_2[Mn_4(O)(OH)(O_2CR)_2L_2]$ to $CO_3^=$ source is in the range of from about 1:1 to about 1:100.

10. The method of claim 9 wherein the $Ba_2[Mn_4(O)(OH)(O_2CR)_2L_2]$ compound is prepared in situ.

11. The method of claim 9 wherein the $Ba_2[Mn_4(O)(OH)(O_2CR)_2L_2]$ is prepared, separated and then combined with the NaCl and source of $CO_3^=$.

* * * * *